US008642355B2

(12) United States Patent
Chen

(10) Patent No.: US 8,642,355 B2
(45) Date of Patent: *Feb. 4, 2014

(54) VERSATILE DRUG TESTING DEVICE

(71) Applicant: Jianfeng Chen, San Ramon, CA (US)

(72) Inventor: Jianfeng Chen, San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,825

(22) Filed: Jun. 25, 2013

(65) Prior Publication Data

US 2013/0295690 A1 Nov. 7, 2013

Related U.S. Application Data

(63) Continuation of application No. 11/853,756, filed on Sep. 11, 2007, now Pat. No. 8,470,609.

(51) Int. Cl.
*G01N 33/543* (2006.01)
*G01N 33/48* (2006.01)

(52) U.S. Cl.
USPC ........... 436/518; 436/524; 436/538; 436/810; 435/7.1; 435/7.2

(58) Field of Classification Search
USPC ........................... 422/412, 417, 430; 436/518
See application file for complete search history.

(56) References Cited

U.S. PATENT DOCUMENTS

| 5,403,551 | A | 4/1995 | Galloway |
| 6,140,136 | A | 10/2000 | Lee |
| 6,379,620 | B1 | 4/2002 | Lee et al. |
| 6,497,843 | B2 | 12/2002 | Tydings |
| 6,514,769 | B2 * | 2/2003 | Lee ............................... 436/518 |
| 6,726,879 | B2 | 4/2004 | Ng et al. |
| 6,805,837 | B2 | 10/2004 | Tydings |
| 6,805,838 | B2 | 10/2004 | Tydings |
| 7,222,547 | B2 | 5/2007 | Alley |
| 8,470,609 | B2 * | 6/2013 | Chen ............................ 436/518 |

* cited by examiner

*Primary Examiner* — Sally Merkling
(74) *Attorney, Agent, or Firm* — Sheppard, Mullin, Richter & Hampton LLP

(57) ABSTRACT

A versatile drug testing device (a lateral flow diagnostic testing device) includes a flat transparent carrier with a top and a bottom with the carrier having a series of independent parallel grooves formed therein running from adjacent to the top to adjacent to the bottom of the carrier, each groove having a first opening and a second opening above the first opening therein adjacent to the bottom of the carrier, at least one drug test strip installed in one of said grooves with its absorbent pad contiguous to the openings and a cover layer attached to the carrier operable to sealing close each of said grooves whereby the bottom of the device can be immersed in a specimen of urine, body fluid, or other biological specimen to wet the pad of the at least one test strip though the ingress of the specimen though the associated openings and the test results on the test strip can be easily viewed through the transparent carrier. Because of the unique construction the device will give accurate reading if temporarily immersed in the specimen or left in the specimen for an extended period of time, making it very user friendly.

18 Claims, 3 Drawing Sheets

VERSATILE DRUG TESTING DEVICE

CROSS-REFERENCE TO RELATED APPLICATIONS

The present application is a continuation application of U.S. Ser. No. 11/853,756, filed Sep. 11, 2007, entitled "Versatile Drug Testing Device," now U.S. Pat. No. 8,470,609, which is incorporated by reference herein.

BACKGROUND OF THE INVENTION

The availability of drugs in the workplace and, in the general population, is pervasive. Employers and others, such as government agencies, general contractors, sports groups and, particularly transportation companies, often utilize drug screening, out of necessity, for both conditions of employment and to ensure safety in the workplace. However, it is impractical to have doctors perform each drug screening on site on a routine basis and also employing a doctor for such tasks is prohibitively expensive.

As a result the various commercial devices have been developed for drug screening in the field (on site) by employers and others which provide near instantaneous test results when liquid samples are collected in such devices. For example, see U.S. Pat. No. 5,403,551 entitled "Assaying Device and Container for In Field Analysis of a Specimen and Later Shipment of the Unadulterated Specimen" issued to Galloway, U.S. Pat. Nos. 6,805,838; 6,805,837; and 6,497,843 issued to Tydings, all entitled "Assaying Device and Method for In-Field Urinalysis". Other patents for such devices included U.S. Pat. No. 6,726,879 issued to Ng et al. See also U.S. Pat. No. 6,140,136 issued to Lee teaching a similar device.

Along with cups the prior art teaches the use of test cassettes, where the test strips lay in a horizontal plane secured to a test bed and the technician places a few drops of a specimen onto the sample area of the individual test strips in the cassette. These test cassettes have reagent test strips attached thereto that change color in the presence of certain chemicals, in this case drugs.

In other embodiments test cassettes can be manufactured so that the ends of the test strips can be submerged into the specimen collection container holding a liquid specimen. These cassettes are often referred to as dippers due to the step, during use, of submerging them in a liquid specimen; see for example U.S. Pat. No. 7,222,547 issued to Alley.

In general the above referenced devices are adapted to bring a small portion of a liquid specimen, such as a urine sample which is collected from an individual, into contact with test strips containing reagents which are responsive to the presence of drugs, such as amphetamines, cocaine, morphine, PCP, THC and/or their metabolites. Typically such reagents include, but are not limited to, colloidal gold coated sheep polyclonal anti-amphetamine, mouse monoclonal anti-benzoyl ecgonine, polyclonal rabbit anti-morphine-3 glucuronide, mouse monoclonal anti-cannabinoid or mouse monoclonal anti-phencyclidine, appropriate drug or drug analog conjugates, and immobilized antisera.

Typically the test strips have a top portion with a selected reagent and an absorbent sample pad at the bottom. Inside the strip are an absorbent membrane and a reaction membrane in communication with the absorbent pad at the bottom. When the absorbent sample pad contacts urine, the urine will wick through the conjugate pad to the reagent (disposed on the reaction membrane) resulting in a positive or negative indication on the surface of the strip; the indication may be one line for positive and two lines for a negative or vice versa, e.g., for large molecule tests such as hormone test, one line is negative, two line is positive. Such test strips are commercially available from companies who have FDA clearance for the same, see FDA web site www.FDA.gov for the names of such companies.

In the past problems have been experienced with flooding of the test strips by the urine samples. Devices such as taught in U.S. Pat. No. 5,403,551 issued to Galloway and also in other patents, use separate compartments to limit the amount of liquid specimen which comes in contact with the test strips. As another example, see U.S. Pat. No. 6,726,879 issued to Ng et al. which uses separate chambers to limit the amount of specimen that comes in contact with the test strips, the patent pointing out that it is highly desirable to limit the contact of a urine sample with the reagent portion of the strips. To this end U.S. Pat. No. 6,397,620 issued to Lee et al., as well as some of the Tyding's patents referenced, supra, employ a vertical surface in a urine collection cup having a wicking membrane disposed thereon so that the wicking membrane conveys urine from the bottom of the cup to the absorbent sample pads of the test strips located at the top of the vertical surface via capillary action. Such arrangements are adapted to avoid flooding the test strip with the urine sample, in that case, which can invalidate the test results.

Problems also exist in situations where an inadequate amount of liquid specimen is absorbed by the test strip. Too little and too much of the specimen can affect the reliability of test results.

Products like the versatile device of this invention, currently in the market place, require the devices to be dipped in the specimen and submerged for a specific time specified by the manufacturer. This dwell time ensures the specimen saturates the wicking pad. The novel device, of the present invention, requires only a quick dip (a second or two) to activate the test, wherefore no dwell time is required to obtain an accurate test.

When specimen volume is limited, products currently available are hard to use. In the novel device of the instant invention a tester can use transfer pipet by adding drops of specimen into an opening in the device to activate the testing with reliable results.

Various prior art devices of the types described above can be viewed at http://www.rapidxams.com, illustrating drug check cups, cassettes and dip or dipper units.

It is an object of the present invention to provide a novel drug testing device which eliminates flooding of the test strips when a carrier containing the strips is submerged in a liquid specimen for either temporarily or for an extended period of time, the submersion time not being critical.

Another object is a provision of a novel drug testing device that ensures more accurate and positive test results when using conventional drug test strips because the novel device requires no required (or specified) submersion period.

In addition the novel device includes a well below its lower opening that serves as a "reservoir" to store enough specimen for a reliable test even after a quick dip in a liquid specimen which feature expedites and simplifies testing making the novel device user friendly.

Still another object is the provision of an improved drug testing device that is economical to construct without sacrificing its drug testing reliability.

Another object is the provision of a construction that insures an adequate sample of a liquid specimen engages each test strip in the device to provide reliable testing without flooding the test strip.

It is also an object to provide an improved drug testing device which can provide reliable test results with limited quantities of a liquid specimen.

It is a general object of the present invention to provide an assaying device which is capable of easily collecting and testing a liquid specimen, such as urine, while avoiding many of the problems experienced by prior art devices now available in the market place.

It is also an object to prove a novel device is constructed of transparent material which provides an improved viewing area of the test strips and which also allows multiple tests to be performed on a single strip (e.g., 2 to 3 test can be performed on a single test strip).

SUMMARY OF THE INVENTION

An improved drug testing device includes a flat transparent carrier with a top and a bottom with the carrier having a series of independent parallel grooves formed therein running from adjacent to the top to adjacent to the bottom of the carrier, with each groove having a first opening and a second opening above the first opening therein in the trough of the groove adjacent to the bottom of the carrier, at least one test strip installed in one of said grooves with its absorbent sample pad contiguous to the openings in its associated groove and a cover layer attached to the carrier in a manner operable to sealing close all of said grooves whereby the bottom of the carrier can be temporarily or permanently dipped into a liquid specimen to wet the sample pad of at least one test strip though the ingress of such specimen through the associated openings and the indications on at least one test strip can be viewed through the transparent carrier.

Typically the test strips are approximately 1.4 mm in thickness and the depth of each groove is about 1.5 mm. As a result the cover layer, when it includes glue on its entire contract surface for attaching it to the carrier 21, will also secure the test strip in its respective groove by adhering to the back of a test strip located in any groove. Further since the width of each groove is only slightly larger than the width of a test strip, the amount of unoccupied volume in each groove with a test strip therein and with the cover layer attached is limited and fluid ingress to the sample pad of the test strip can only occur through the two openings porting each groove.

Of course the carrier can have multiple test strips and as many independent grooves as desired as long as the number of grooves does not make the carrier too cumbersome to use in the field.

BRIEF DESCRIPTION OF THE DRAWINGS

The above-mentioned features and objects of the present invention are illustrated in the following description taken in conjunction with the accompanying drawings wherein like reference numerals denote like elements and in which.

DETAILED DESCRIPTION OF THE INVENTION

Figure 1:
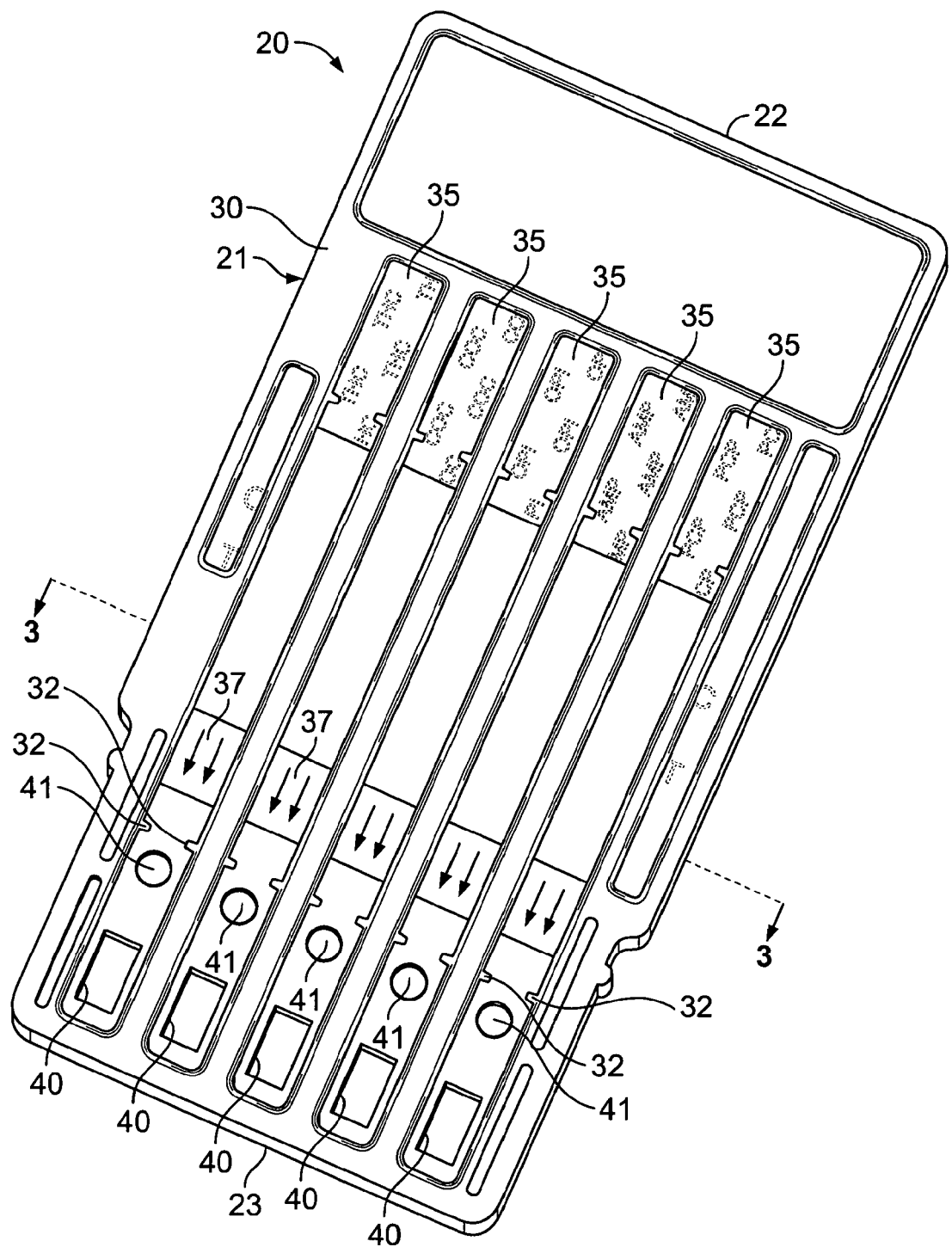
FIG. 1. is a perspective of the novel drug testing device with the end cap removed illustrating its principal components.
Figure 2:
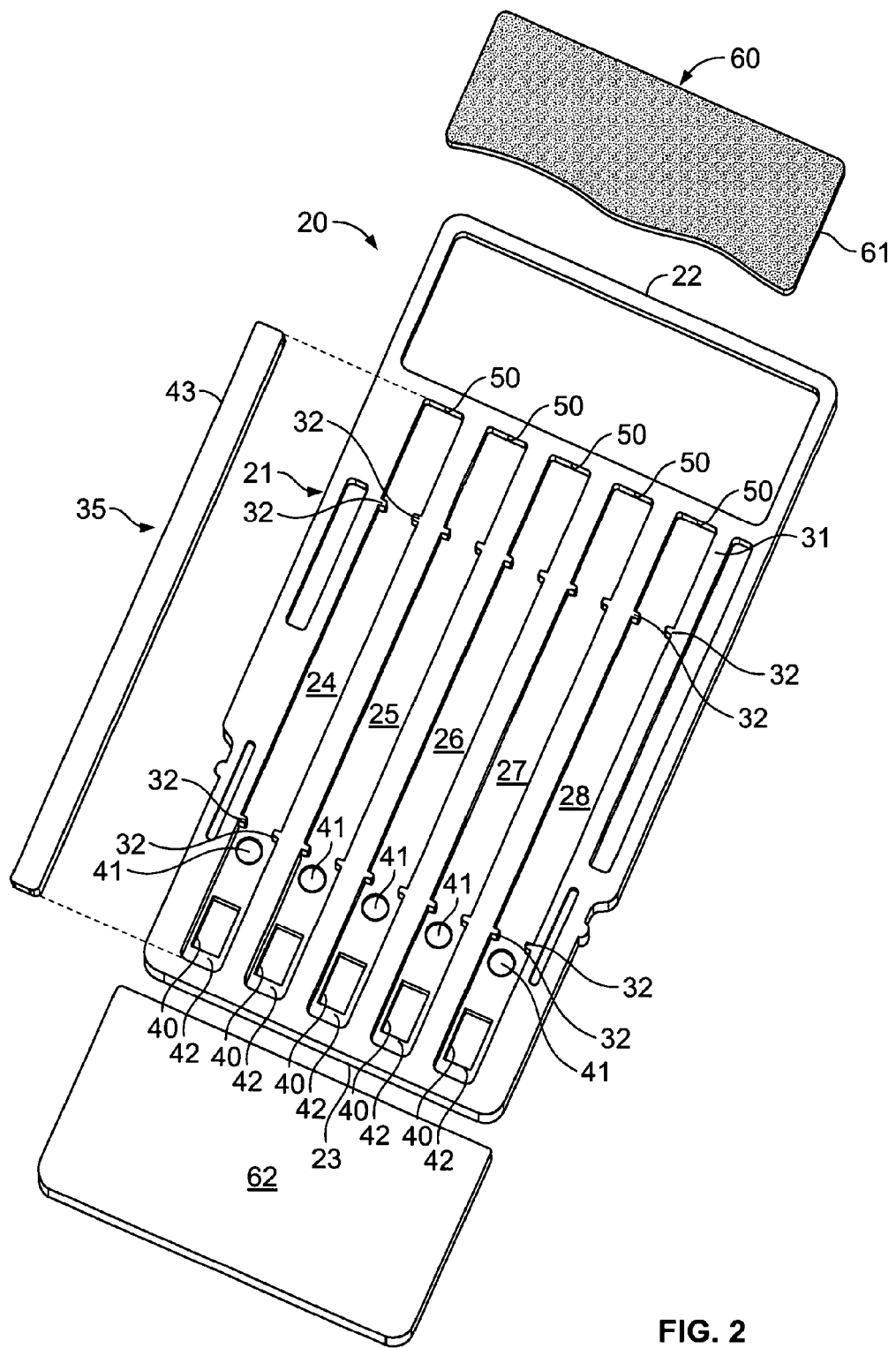
FIG. 2 is a an exploded perspective of the device shown in FIG. 1 illustrating the construction of device.

Referring to FIG. 1 the novel drug testing device 20 is illustrated. It includes a transparent rectangular carrier 21 having a front face 30, a back face 31, a top 22 and a bottom 23. As can be seen in FIG. 2, the transparent carrier has a series of independent, parallel grooves 24, 25, 26, 27 and 28 formed in its rear or back face 31 which extend from a point adjacent to the top of the carrier to a point adjacent to the bottom of the carrier. While only five grooves are illustrated, the carrier can include more or less grooves depending on the number of test strips 35 which are to be employed. In FIG. 1 the test strips 35, one assembled in each groove, are easily viewable through the transparent carrier which can be injection molded. In addition, each groove includes opposed lugs 32 extending into the groove near the top and bottom ends of the groove. These opposed lugs squeeze the sides of test strips when installed enough to maintain the location of the test strips in its associated groove when the unit is assembled.

The front face 30 of the carrier 20 is smooth, except for the two openings in each groove (grooves 24, 25, 26, 27 and 28). The base opening 40 of each groove is located adjacent to the bottom 23 of the carrier 20 where it has fluid communication with its associated groove. It is shown as a rectangular window in the FIGS. 1 and 2. Just above the base opening is a bleed port 41, which is typically a round aperture, which also has communication with its associated groove and is located between 4 and 6 mm above the top of the base opening.

The presence of base opening 40 and its adjacent bleed port 41 is important to the proper functioning of novel device 20. In this regard, when the device 20 is completely constructed, as hereinafter described, and submerged into a liquid specimen or sample, a portion of the specimen will ingress though the base opening and trapped air at the bottom of the groove will bleed or vent through the bleed port ensuring the sample pad 44 (see FIG. 4) of the test strip 35 contiguous to these opening is fully wetted with the specimen. Such wetting of the sample pad of the test strip occurs almost instantaneously in the current device and it is not necessary for a user to be critical of the time that the bottom of the carrier is submerged in the liquid specimen nor the actual depth of the bottom 23 of the carrier in the specimen which are often critical requirements in the prior art devices. Such prior art devices typically have markings thereon for the insertion depth of the unit and specify the time for the unit to be submerged to obtain a reliable test.

In the novel device 20 of this invention, its improved function is achieved by a differential of pressure of the liquid at the bleed port and the base opening when the bottom 23 of the carrier 21 is submerged in a specimen. This differential can be generalized as, at the base opening the pressure is P1=H1*D (depth of window opening in the fluid×density of fluid) and at the bleed port the pressure is P2=H2*D (depth of the aperture in the fluid×density of the fluid). As H2 is smaller than H1 there is a differential which can be expressed as ▲AP=P1−P2. As a result, the higher pressure at the base opening will cause fluid to enter the groove and expel any trapped air through the bleed port for better wetting of the absorbent sample pad of a test strip. As a result the novel device of this invention is more reliable than prior art devices of a similar type because it is more user friendly and requires less rigorous attention to detail when it is employed.

In addition, since the base opening 40 is several millimeters, from 2 to 4 millimeters, above the bottom of its associated groove, there is a small well 42 formed thereat, which will rapidly fill while a portion of the liquid specimen when the bottom 23 of the carrier 20 is submerged. While only a very small amount of specimen is trapped in the well, it is enough to activate the reagent on the test strip for a positive test, should inadequate wetting otherwise occur, such as may occur due to the surface tension of the specimen.

Referring FIG. 2, the exploded view of the components, the back –31 of the carrier 20 is shown where the parallel grooves 24, 25, 26, 27 and 28 are depicted formed in the transparent carrier. It is obvious that these grooves are closed at their top end 50 and bottom end 51 and that the base opening 40 is formed in the trough of each groove slightly above the bottom end of the carrier. Slightly above the base opening is the bleed port 41 which is typically between 3 to 6 millimeters above the base opening. The base opening is typically a rectangular opening with dimensions of 5 to 6 millimeters by 2 to 5 millimeters. If the bleed port is a circular aperture is will have a diameter from 2 to 4 mm.

Into the several grooves 24, 25, 26, 27 and 28 a drug test strip 35 is inserted so that its sample pad 44 is contiguous to the base opening and bleed port. If desired a spacing layer 37 can be added to the face of the test strip to increase the thickness of the test strip just above the location of the sample pad contiguous to the base opening and the bleed port. The purpose of this layer is to limit the amount of specimen that travels up the groove by increasing the thickness of the test strip in this area to block the ingress of the liquid specimen and trap the air above the spacing layer, both of which prevents flooding of the test strip in the associated groove.

Figure 4:
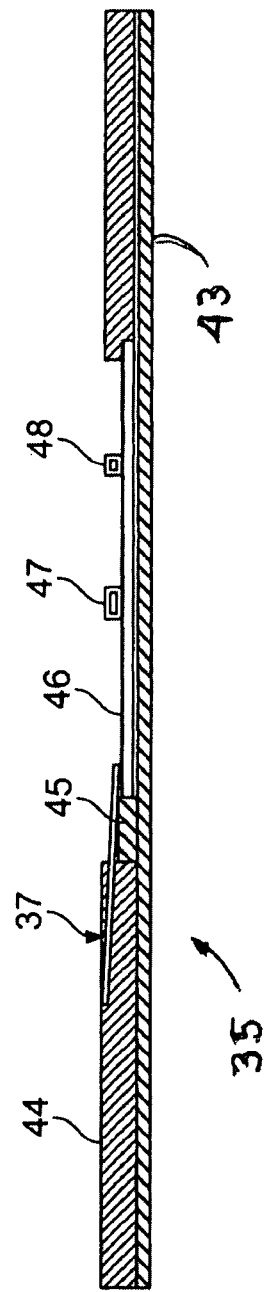
FIG. 4 is a cross-section of a test strip that can be employed with the current device.

Referring now to FIG. 4 illustrating a typical test strip 35, it can be seen that it has a vinyl backing 43 on which an absorbent sample pad 44 is secured that feeds liquids deposited thereon by capillary action to a conjugate pad 45 that communicates with a membrane 46 on which a test reagent 47 and a control reagent 48 are located. Also illustrated on the test strip is a spacing layer 37 which function has been described previously.

Again referring to FIG. 2 it can be seen that each of the test strips 35 employed is placed in an associated groove, and thereafter the cover or backing layer 60, having its contact surface 61 covered with glue, is assembled on the back 31 of the transparent carrier 20 so that it completely seals each groove whereby the only ingress to the test strip is through the base opening 40 and the bleed port 41 associated with each groove. In addition the cover or backing layer 60 will contact the back of the test strip placed in any of the grooves, securing the strips in place. When the cover of backing layer is glued to the back of each test strip in the assembled device, it is difficult to tamper (remove or change) any of the test strips without destroying the novel device. However, in place of glue the backing layer can be welded to the back of the carrier 21 to seal the opening of each of the grooves on the back face of the carrier.

Figure 3:
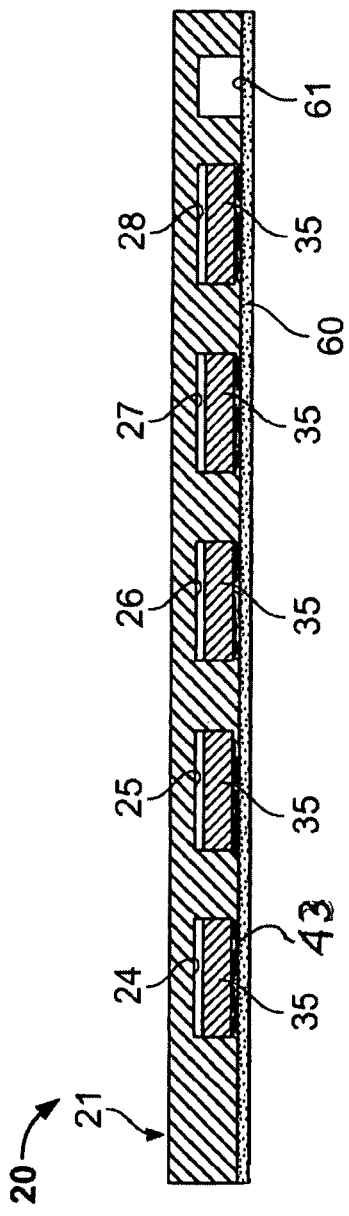
FIG. 3 is a cross-section along line 3-3 shown in FIG. 1.

In the cross section shown in FIG. 3 it can be seen that test strip 35 takes up the majority of the volume of its associated groove when the cover or backing layer 60 closes the groove. As a result flooding of the test strip with the urine specimen will not occur due to trapped air above the spacing layer 37.

The location of the bleeding vent is designed and calculated depending on the size of the device. It is always below the gold conjugate pad 45 (see FIG. 4) so that fluid can enter the lower opening, wet the absorbent pad 44 to activate the testing process. The air pressure in the groove above the bleeding port will prevent the liquid from flowing further into the groove and above. Due to this limitation the delivery of the specimen above the bleeding port is through capillary action and is thus controlled. The groove cross-section, lower opening, bleeding port size and location, test strip specifications, are all correlated and designed.

As indicated the test strips employed in this novel device are conventional and can be purchased from various manufacturers.

When not in use, a cap 62 is used to enclose the bottom of the carrier 20 to avoid contamination of the test strips 30. However, in the current design contamination of the test strips is less likely because the sample pads thereof are completely enclosed in the carrier, as illustrated.

Cap 62 is used to enclose the bottom of the carrier 21 that contacts specimen after testing process to avoid contamination. Cap 62 can have two projections A and B (not shown) that extend from the opening of the cap and form guides to assist in assembling the cap on the bottom of the carrier 20 to make it more user friendly.

Having described my invention, I claim:

1. A device comprising:
   a carrier having a plurality of groove formations in a face of the carrier, wherein the plurality of groove formations are formed such that, in operation, the plurality of groove formations receive test strips therein;
   a base opening at a first position in the face of the carrier within a first groove of the plurality of groove formations, wherein, in operation, a sample pad of a first test strip in the first groove is exposed to a fluid in contact with the face of the carrier through the base opening;
   a bleed port at a second position above the first position in the face of the carrier within the first groove, wherein, in operation, the sample pad of the first test strip in the first groove is exposed through the bleed port to the fluid;
   wherein, in operation, when the carrier is submerged in the fluid, a first fluid pressure existing at the base opening and a second fluid pressure existing at the bleed port, the first fluid pressure being greater than the second fluid pressure, a fluid pressure difference between the first fluid pressure and the second fluid pressure causing the ingress of a portion of the fluid through the base opening and the expelling of air between the base opening and the bleed port through the bleed port.

2. The device of claim 1, wherein a back face of the carrier is transparent and rectangular and the plurality of grooves include independent parallel grooves.

3. The device of claim 1, further comprising opposed lugs on a first side of the first groove and a second side of the first groove, wherein, in operation, the opposed lugs engage sides of the first test strip received in the first groove to hold the first test strip in place.

4. The device of claim 1, wherein the first position is disposed above a bottom of the carrier, a portion of the face of the carrier between the bottom of the carrier and the first position forming a side of a well, the well, in operation, containing a volume of the fluid that activates a test reagent on the first test strip in the event of a positive test.

5. The device of claim 1, wherein, in operation, the first test strip includes a spacing layer disposed above the bleed port, the spacing layer reducing an amount of the fluid that is displaced within the first groove above the bleed port.

6. The device of claim 1, further comprising a backing layer affixed to the carrier and contacting a back of the first test strip, the backing layer sandwiching the first test strip between the face of the carrier and the backing layer.

7. The device of claim 1, further comprising a cap configured to receive a bottom end of the carrier, the cap being of a size such that the bleed port and the base opening are contained within the cap when the cap fully receives the carrier.

8. The device of claim 1, further comprising means for sealingly closing the first groove along a back face of the carrier, the back face of the carrier opposing the face of the carrier.

9. A method comprising:
collecting a volume of a fluid within a sample holding receptacle;
submerging a carrier in the fluid contained within the sample holding receptacle, the carrier comprising:
  a plurality of groove formations in a face of the carrier, wherein a first groove of the plurality of groove formations includes a first test strip therein;
  a base opening at a first position in the face of the carrier within the first groove of the plurality of groove formations, wherein a sample pad of the first test strip in the first groove is exposed to the fluid in contact with the face of the carrier through the base opening;
  a bleed port at a second position above the first position in the face of the carrier within the first groove, wherein, in operation, the sample pad of the first test strip in the first groove is exposed through the bleed port to the fluid;
  wherein, in operation, submerging the carrier in the fluid causes a first fluid pressure to exist at the base opening and a second fluid pressure to exist at the bleed port, the first fluid pressure being greater than the second fluid pressure, a difference between the first fluid pressure and the second fluid pressure causing the ingress of a portion of the fluid through the base opening and the expelling of air between the base opening and the bleed port through the bleed port.

10. The method of claim 9, further comprising affixing a backing layer to the carrier, the backing layer contacting a back of the first test strip and sandwiching the first test strip between the face of the carrier and the backing layer.

11. The method of claim 10, wherein the backing layer is glued to the carrier.

12. The method of claim 10, wherein the backing layer is welded to the carrier.

13. The method of claim 9, further comprising engaging the carrier with a cap, the cap configured to receive a bottom end of the carrier, the cap being of a size such that the bleed port and the base opening are contained within the cap when the cap fully receives the carrier.

14. A method comprising:
collecting a volume of a fluid within a sample holding receptacle;
submerging a carrier in the fluid contained within the sample holding receptacle, the submerging causing a well to form between the carrier and the sample holding receptacle, the carrier comprising:
  a plurality of groove formations in a face of the carrier, wherein a first groove of the plurality of groove formations includes a first test strip therein;
  a base opening at a first position in the face of the carrier within the first groove of the plurality of groove formations, a sample pad of the first test strip in the first groove being exposed to the fluid in contact with the face of the carrier through the base opening;
  a bleed port at a second position above the first position in the face of the carrier within the first groove, wherein, in operation, the sample pad of the first test strip in the first groove is exposed through the bleed port to the fluid;
trapping a portion of the volume of fluid in the well, the portion of the volume of fluid being large enough to activate a test reagent on the first test strip in the event of a positive test.

15. The method of claim 14, further comprising affixing a backing layer to the carrier, the backing layer contacting a back of the first test strip and sandwiching the first test strip between the face of the carrier and the backing layer.

16. The method of claim 15, wherein the backing layer is glued to the carrier.

17. The method of claim 15, wherein the backing layer is welded to the carrier.

18. The method of claim 14, further comprising engaging the carrier with a cap, the cap configured to receive a bottom end of the carrier, the cap being of a size such that the bleed port and the base opening are contained within the cap when the cap fully receives the carrier.

* * * * *